(12) United States Patent
Schmelzer

(10) Patent No.: US 6,636,315 B2
(45) Date of Patent: Oct. 21, 2003

(54) METHOD FOR ESTIMATING THE QUALITY OF DISTRIBUTION OF PIGMENTS IN A MATRIX

(75) Inventor: Josef Schmelzer, Cologne (DE)

(73) Assignee: Kronos International, Leverkusen (DE)

( * ) Notice: Subject to any disclaimer, the term of this patent is extended or adjusted under 35 U.S.C. 154(b) by 97 days.

(21) Appl. No.: 09/931,955

(22) Filed: Aug. 17, 2001

(65) Prior Publication Data

US 2002/0048022 A1 Apr. 25, 2002

(30) Foreign Application Priority Data

Sep. 1, 2000  (DE) .......................... 100 43 038

(51) Int. Cl.⁷ ................................ G01J 3/50
(52) U.S. Cl. ...................... 356/425; 356/336
(58) Field of Search ...................... 356/425, 402, 356/405, 336, 335; 250/226

(56) References Cited

U.S. PATENT DOCUMENTS

| | | | |
|---|---|---|---|
| 3,916,168 A | * | 10/1975 | McCarty et al. ............ 356/405 |
| 4,887,217 A | | 12/1989 | Sherman et al. |
| 5,137,364 A | | 8/1992 | McCarthy |
| 5,231,472 A | | 7/1993 | Marcus et al. |
| 5,929,998 A | * | 7/1999 | Kettler et al. ............... 356/405 |
| 6,064,487 A | * | 5/2000 | Kettler et al. ............... 356/402 |

FOREIGN PATENT DOCUMENTS

| | | | |
|---|---|---|---|
| CH | 389284 | | 7/1965 |
| DE | 2805511 A1 | * | 8/1978 |
| DE | 3929172 | | 3/1991 |
| GB | 1589705 | | 5/1981 |

OTHER PUBLICATIONS

Pigment Handbook, Vol. 1, Edited by Peter A. Lewis (1988, Wiley Interscience Publications), pp. 1–42 (Titanium Dioxide).*

* cited by examiner

Primary Examiner—Richard A. Rosenberger
Assistant Examiner—Vincent P. Barth
(74) Attorney, Agent, or Firm—Rodney T. Hodgson

(57) ABSTRACT

The quality of distribution of pigments in a matrix is estimated by measuring the reflectivity of a sample of the pigmented matrix at a shorter and a longer wavelength, and calculating a function of the two measurements. A ratio of the normalized reflectivity for broad short and long wavelength bands is the preferred function.

17 Claims, 8 Drawing Sheets

METHOD FOR ESTIMATING THE QUALITY OF DISTRIBUTION OF PIGMENTS IN A MATRIX

CROSS REFERENCE TO RELATED APPLICATIONS

This application claims priority pursuant to Title 35, United States Code, Section 119(a)-(d) or (f), or 365(b) to the German Application Number 100 43 038.4 filed Sep. 1, 2000, by the same inventor, where the above named application is hereby incorporated herein by reference in its entirety including incorporated material.

FIELD OF THE INVENTION

The field of the invention is the testing of dispersion of particles and pigments in liquid and solid matrices.

BACKGROUND OF THE INVENTION

The purpose of coatings is to protect and enhance the appearance of surfaces. Therefore, numerous methods have been developed for testing the properties of coatings. In the optical field, these include gloss and haze measurements, color measurements, determination of the contrast ratio or the determination of scattering coefficients. In the case of TiO2 pigments, these methods provide an indirect statement concerning the quality of distribution of these pigments in the polymer matrix. The finer the pigment particles are, and the more uniformly they are distributed in this matrix, the better will be the hiding power or the contrast ratio, the higher the gloss value, the lower the haze value and the greater the brightness. Electron micrographs of microsections of paint films provide a direct insight into the state of dispersion of the pigment in the coating. In practice, measurements are sometimes obtained for which there is no simple explanation. For instance, when used in a familiar formulation, a time-proven TiO2 pigment may produce a weaker contrast ratio in one production run that it did in a previous run, although the brightness and gloss values remain unchanged. The fault could lie in the formulation, the preparation of the coating, the dispersion process or the test method. Questions of this kind also arise when developing formulations. Does the pigment tend towards flocculation in one binder and towards finer distribution in another? What is the effect on the particle size distribution if the dispersing agent concentration is increased or reduced? The prior art is deficient in that It would take too much time and expense to answer these questions with the help of electron micrographs. Prior art methods of measuring pigment distribution by measuring transmission of light through the pigment matrix mix noted in U.S. Pat. Nos. 6,236,460 and 6,040,913 are deficient in that transparent substrates must be used and uniform thicknesses of thin material is necessary. The present invention is a method that permits the quick and simple observation of changes in the distribution of the pigment in the polymer matrix.

OBJECTS OF THE INVENTION

It is an object of the invention to provide a method of simply measuring the quality of dispersion or distribution value of pigment particles in a matrix. It is an object of the invention to provide a method of comparing one pigment dispersion sample with another. It is an object of the invention to provide a method of estimating pigment floculation. It is an object of the invention to provide a method of testing different matrices with the same pigment mix.

SUMMARY OF THE INVENTION

The present invention is a system, apparatus and method to measure the reflectivity of a sample of pigment dispersed in a solid or liquid matrix in at least two wavelength bands, and to determine the quality of the dispersion by calculating a function of the measured reflectivities. The most preferred embodiment of the invention is to measure the reflectivity $F_1$ and $F_2$ integrated over two broad bands of wavelengths $\lambda_1-\lambda_m$ and $\lambda_n-\lambda_2$, and to derive a quality factor S proportional to the quotient $F_1/F_2$.

BRIEF DESCRIPTION OF THE DRAWINGS

FIG. 5 shows distribution values of pigments A, B and C in

FIG. 5 shows distribution values of pigments A, B and C in Bayhydrol D155 and Larodur BX 150

DETAILED DESCRIPTION OF THE INVENTION

Information on the state of dispersion of a TiO2 pigment in a coating can be derived from the scattering coefficient according to the method of Kubelka, P., and Munk, F. reported in Z. techn. Phys. 12 (1931), p. 593–601. The theory behind this measurement was developed at a time when three-filter photometers alone were used for reflectance measurements. These photometers yield the so-called chromaticity coordinates (DIN 5033, Part 3) X, Y and Z. These are integral mean values of the colour stimuli of the light reflected by the test object, as detected by the photometer. The higher the value of the scattering coefficient, the greater the number of scattering centres contained in the coating under test, i.e. the better the state of dispersion. However, determination of the scattering coefficient is a fairly complex process, which is why the search for a simpler method began. The present development of spectrophotometers has made it possible to measure reflectance values in intervals of 10 nm over a measuring range greater than 380 nm to 720 nm. Improvements in light emitting diodes (LED'S) and various semiconductor and other solid state lasers such as organic lasers and LED's have also lead to possibilities of accurate spectrally resolved photometry using lighter and less costly methods. At the same time, according to Mie, G in Ann. Physik 25 (1908), 377 and Gans, R.: Ann. Physik 37, 881 (1912), the wavelength of monochromatic light and the particle diameter at which this light is optimally reflected are interdependent. As a rough approximation, it can be said that a particle of diameter a optimally reflects light with a wavelength of 2a. For a given diameter distribution of the pigment particles in a matrix, this means that a high proportion of fine particles will result in high reflectance being measured in the short-wave range, while a high proportion of coarse particles will produce high reflectance in the long-wave range. In this case, the reflectance curve obtained with a spectrophotometer would be a distorted map of the particle size distribution of the pigment in the wavelength interval measured. This interval is referred to below as the "optical interval". As a result, changes in the state of distribution of the pigments in the solid matrix—due to different intensities of dispersion, flocculation, agglomeration, etc.—can be tracked by measuring the reflectance curves.

Experimental tests principally used reflectance curves of the coatings doctor bladed or sprayed on white porcelain tiles and on white primed aluminum plates. These coatings fulfil the requirements of DIN 53164, according to which the difference in the brightness values (Y-values), measured over a white-coated, white tile and over a white-coated, black tile, may only be between 2 and 6 brightness points. These films can thus be regarded as approximately optically opaque. Table 1 lists the experimental conditions.

Figure 3:
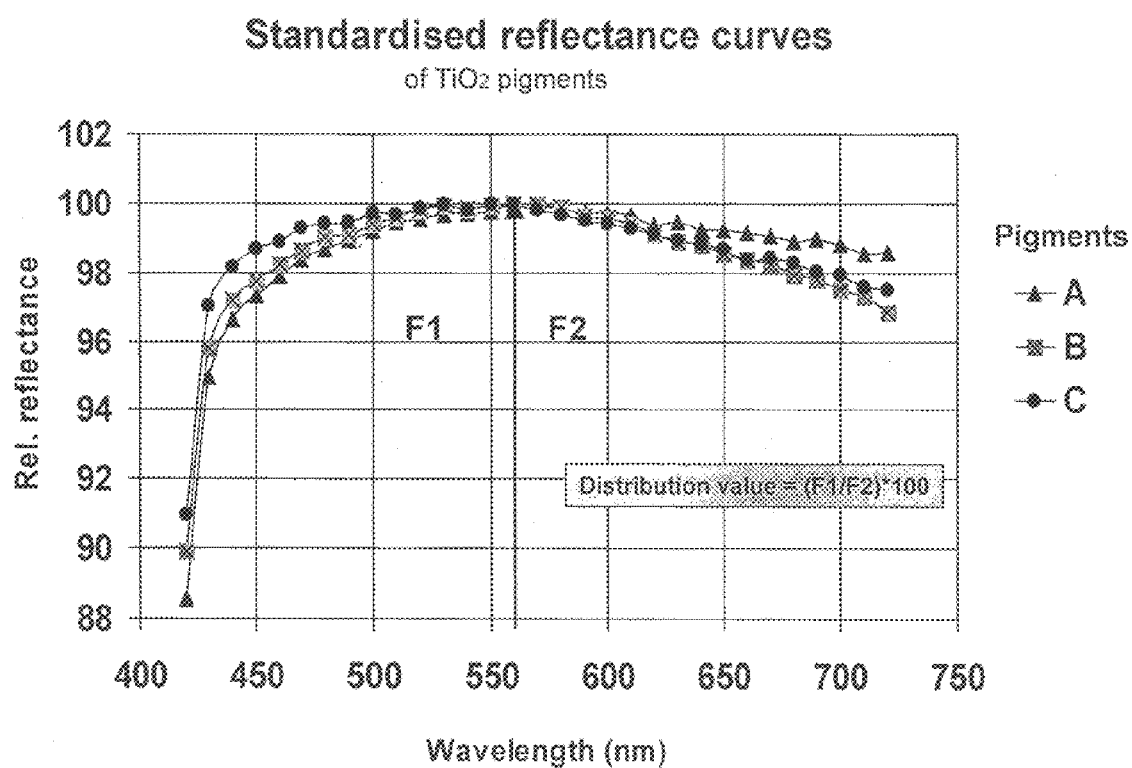
FIG. 3 shows standardized reflectance curves of pigments A, B and C

FIG. 3 shows the standardised reflectance curves of pigments A, B and C. It can be seen that the coating pigmented with pigment C has higher reflectance values in the short-wave wavelength range below 560 nm. than the other two coatings, relative to the curve maximum In turn, the paint film containing pigment B displays higher relative reflectance values in this range than the film produced with pigment A. In contrast, the coatings pigmented with pigment C have relatively low reflectance values in the long-wave range greater than 560 nm. Even lower reflectance can be seen for the paint film containing pigment B. The film with pigment A yields the highest relative reflectance values in the long wavelength range.

If it is assumed that the reflectance value at a certain wavelength roughly corresponds to the number of particles that reflect this wavelength best, ten the area under the short-wave part of the curve ($F_1$) corresponds to the number of relatively fine particles and the area under the long-wave part of the curve ($F_2$) to the number of relatively coarse particles. The relative reflectance curves of FIG. 3 have been

TABLE 1

Description of the test conditions

| | |
|---|---|
| Measuring apparatus: | TCM spectrophotometer, standardised illuminant C, Byk Gardener |
| | Color View, standardised illuminant C, Byk Gardener |
| Measuring range: | 380 nm to 720 nm |
| Substrates: | White porcelain tiles, white-primed aluminium panels |
| Formulations based on: | Bayhydrol D155/Resimene 745, Larodur 150 BX/Cymel 327 (Cymel 1156) |

| TiO$_2$ pigments: | A | B | C |
|---|---|---|---|
| Diameter: | | | |
| Numerical mean: | 0.27 μm | 0.21 μm | 0.20 μm |
| Mass mean. | 0.43 μm | 0.34 μm | 0.37 μm |

| | |
|---|---|
| PVC: | D, E and trial pigments (TP) |
| | Bayhydrol D155: 10%, 24% |
| | Larodur 150 BX: 24% |
| Film thicknesses: | Porcelain tiles: 30–40 μm; corresponds to the test requirements for Y-values (brightness) to DIN 53164. |
| | Glass plates: opaque films |
| | Aluminium panels: opaque films |
| Application: | Porcelain tiles and glass plates: draw-down |
| | Aluminium panels: spray |

Figure 1:
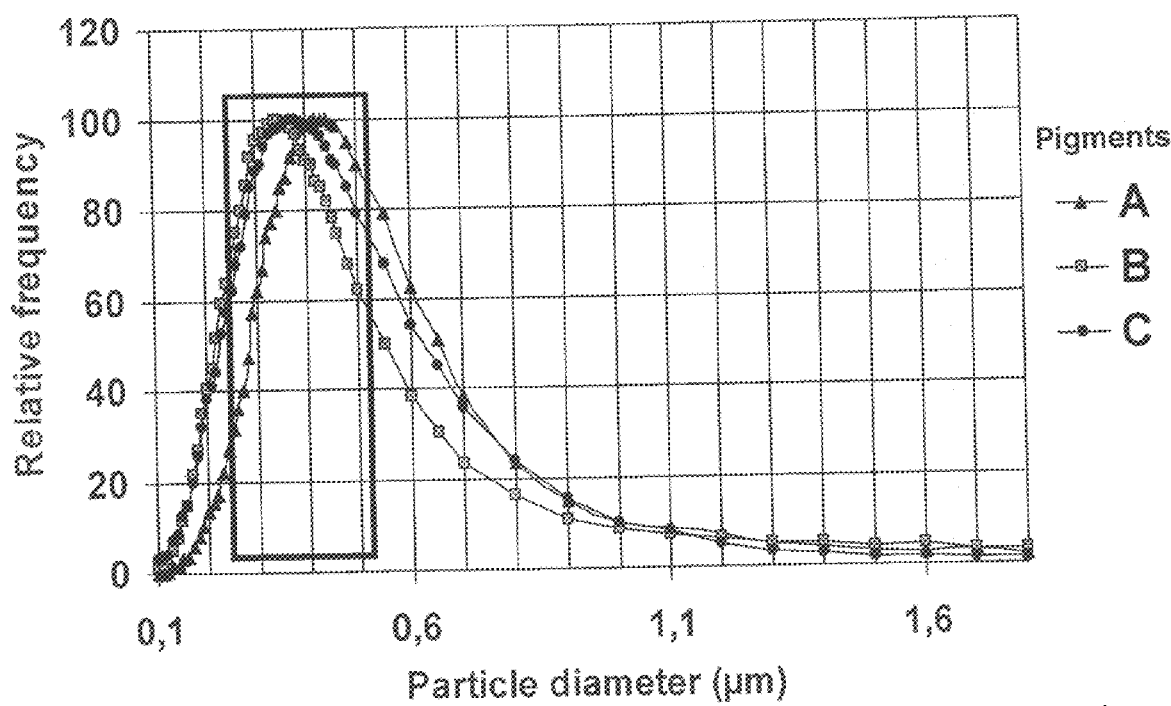
FIG. 1 shows particle size distribution curves (mass distributions) of pigments A, B and C

FIG. 1 shows the particle size distribution curves (mass distributions) of pigments denoted A, B and C. If the mass mean is taken as the basis for assessment (see Table 1), the resultant order of the mean diameters is A>C>B. Based on the numerical mean A>B≧C.

Figure 2:
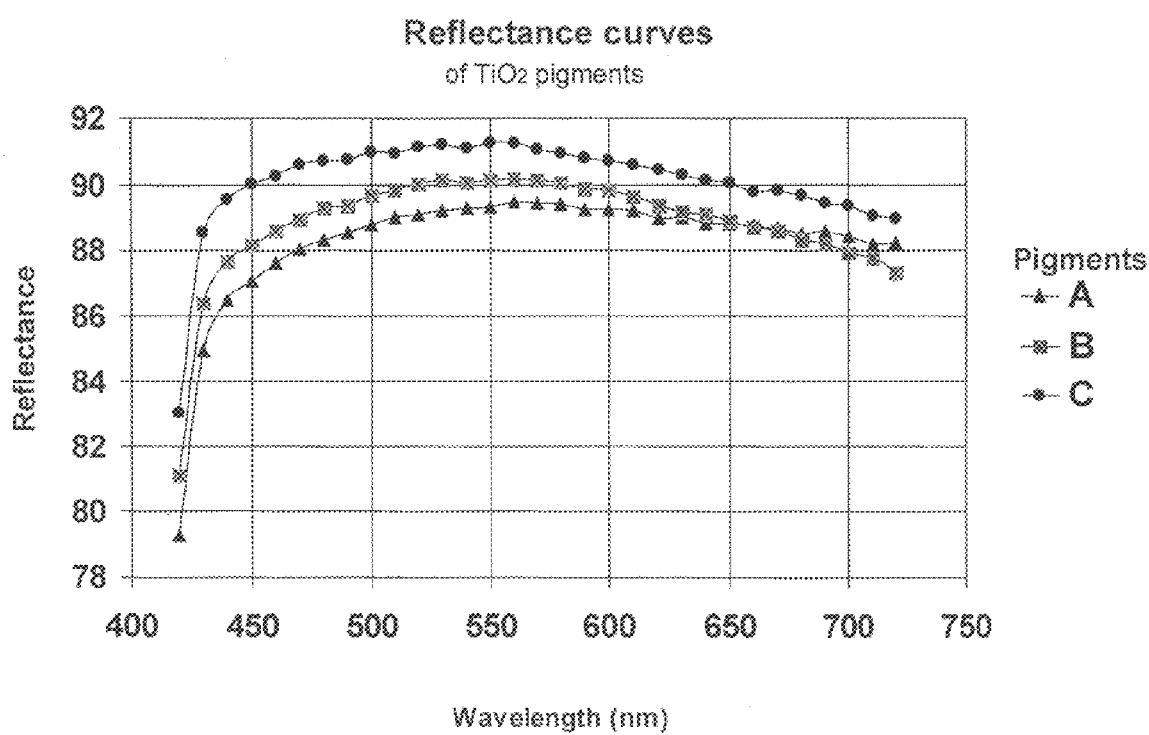
FIG. 2 shows reflectance curves of pigments A, B and C in a coating with PVC=24%.

On examining the particle size distribution curves in the range between 0.2 μm and 0.4 μm, as shown in FIG. 1, it can be seen that the average particle size is smaller for pigments B and C than for pigment A. Reflectance curves in FIG. 2 of pigments A, B and C in a coating with pigment volume concentration (PVC)=24% show that the total reflectance of the three coatings is very different over almost the entire wavelength range. This means that, in addition to differences in the intensity of reflectance caused by different particle concentrations in the respective range, light absorption will also play a role, e.g. due to different contents of trace elements with a colouring effect. If the reflectance curves illustrated are to be compared independently of light absorption, they have to be standardised. In the case in hand, the maxima of the reflectance curves are at 560 nm, and the reflectance value at 560 nm was defined as the value 100.

arbitrarily divided at 560 nm, and the broad band short wavelength reflectance $F_1$ has been defined to be the integral of the reflectance curve from the minimum wavelength measured at 380 nm to 560 nm, while the long wavelength reflectance $F_2$ has been defined to be the integral of the reflectance curve front 560 nm to 720 nm. The most preferred embodiment of the invention is to use two broadband measurements of reflectivity at short and longer wavelengths, and to construct a function of the two measurements which may be used to compare different pigment batches, different binders, etc. In general, the wavelengths measured for the short wavelength band will be from $\lambda_1$ to $\lambda_m$ and from $\lambda_n$ to $\lambda_2$, for the long wavelength band, where $\lambda_1 < \lambda_m$, $\lambda_n < \lambda_2$. In the most preferred embodiment, $\lambda_m = \lambda_n$ is the maximum of the reflectance curve, but in general $\lambda_m$ may be longer or shorter than $\lambda_n$. For narrow wavelength band illumination by lasers values of $\lambda_1$ shorter than 440 nm and $\lambda_2$ longer than 900 nm are preferred embodiments. The ratio $S = (F_1/F_2) * 100$ is a measure of the relative fineness of the pigment distribution in a given coating in the optical interval covered. This value S is referred to below as the "distribution value". Of course, other functions of the reflectivity at two or more wavelengths may be used, but the simple ratio is the least complicated and works well to describe the total effect of the particle distribution and the dispersion of the particles into the matrix.

While the examples shown are measured with paint doctor bladed or sprayed on to substrates, other methods of preparing the samples could be used. In particular, the coating may be measured when still wet, and in particular, the liquid slurry may be measured while it is still being mixed by measuring the reflectivity of the surface of a pot full of paint.

A preferred embodiment of the invention is to use a portable device which uses filters to determine the different bandwidths directed on to the sample or to resolve white light reflected from the sample. Another preferred embodiment is to use a two or more light emitting diodes or laser devices to produce light with well defined wavelengths and bandwidths, and to determine the reflectivity at shorter and longer wavelengths to define and to determine the distribution value of such pigments. A preferred embodiment measures the distribution value of a standard surface, then the distribution values of test pigments and matrices may be compared with the standard.

The benefit of a test method depends not only on the nature of the data obtained, but also on its simplicity and accuracy. In order to examine the accuracy and repeatability of the method, pigments A, B and C were each measured 42 times in a formulation with a PVC of 24% and 24 times in one with a PVC of 10%.

It was found that the distribution values can be distinguished from one another sufficiently well for practical application, if four values are used after eliminating any outliers.

Figure 4:
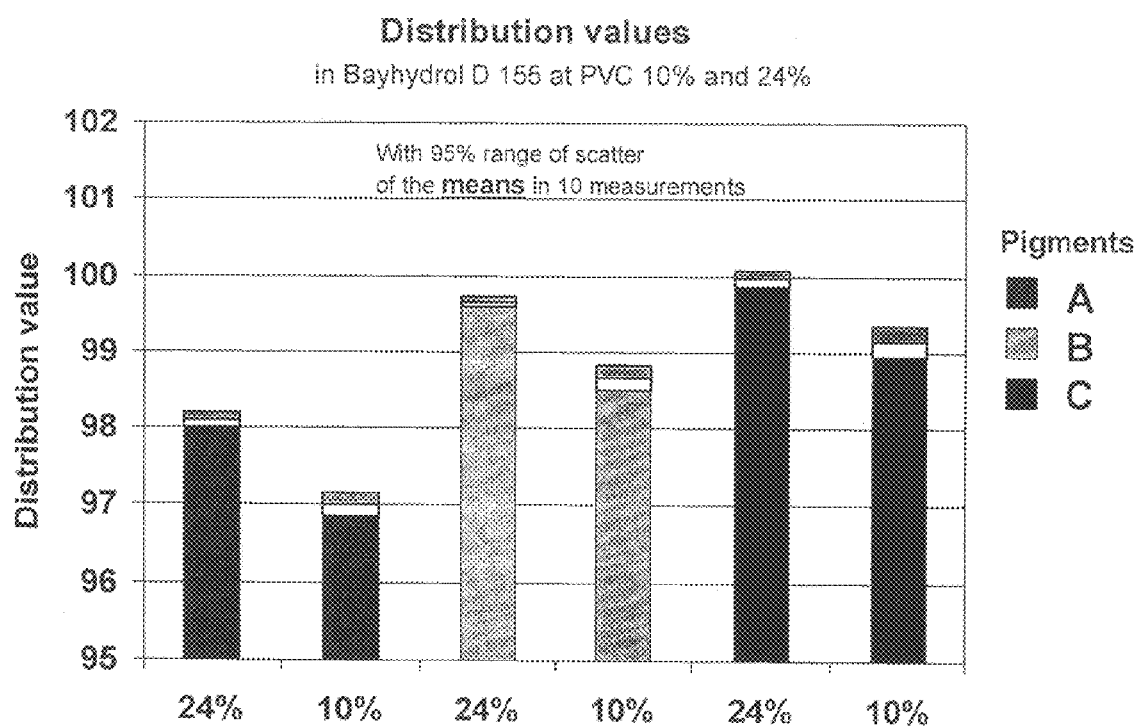
FIG. 4 shows distribution values of pigments A, B and C in Bayhydrol D155.

FIG. 4 shows the distribution values of a white, water-borne paint based on pigments A, B and C in Bayhydrol D155 at PVC=10% and 24%, showing the 95% range of scatter of the means of 10 individual measurements on the polyester/melamine resin.

As it was found that the distribution values of the wet paints changed after storage for several days, only the 10 measurements of the first day of the test were used to calculate the 95% range of scatter. It can be seen that the distribution values of the pigments increase from A to B to C for both PVCS. By definition, increasing distribution values mean higher fines contents in the particle size distributions. This assessment of the pigment particle size distributions matches the numerical means from the sedigraph measurements. Moreover, the distribution values for the lower PVC of 10% are lower than those for the higher PVC throughout.

Figure 5:
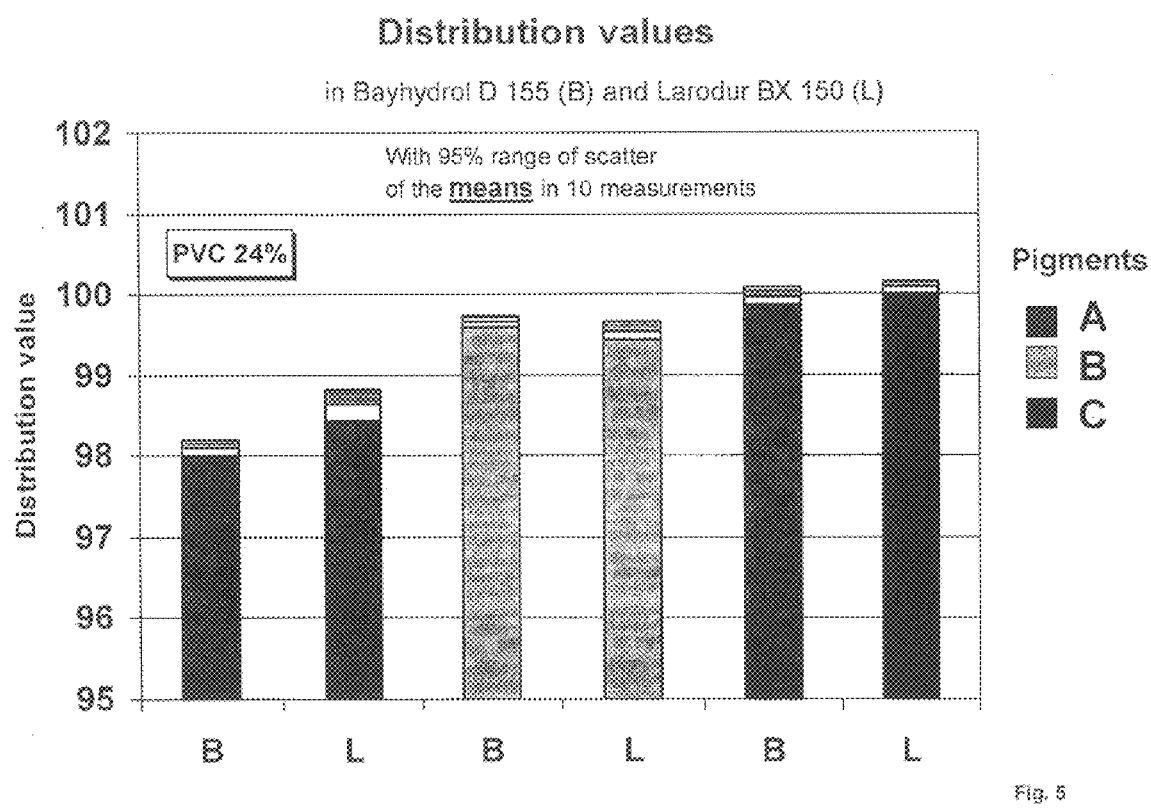

FIG. 5 illustrates the distribution values in a polyester/melamine resin and an acrylic/melamine resin coating (Bayhydrol D155 and Larodur BX 150) with a PVC of 24%. The order of the pigments in terms of increasing fines content (distribution value) is A, B, C in both binder systems at a PVC of 24%.

How can the higher distribution values for a PVC of 24% compared to 10% be interpreted? The ratio of "fine" to "coarse" would normally be expected to remain unchanged when the concentration is increased. In fact, however, aggregation of the pigment particles, e.g. in the form of floccules or agglomerates, increases at the higher concentration, or primary particles occur which simply lie closer together and which the light thus detects as being single particles. The result of this is that a number of particles disappear from the upper reflectance range (>720 nm) because of the excessive particle size. On the other hand, particles are also added to this range due to the aggregation of "fine" particles. The particle concentration in the "fine" range is increased again by the aggregation of even finer, previously undetected particles (<380 nm). On balance, the concentration in the "fine" range apparently increases more than in the "coarse" range, meaning that the distribution value rises.

The systematically higher distribution values for PVC=24% compared to PVC=10% mean that the distribution values, and thus also the particle size distribution curves, are dependent on the PVC.

In addition to the PVC effect of the TiO2 pigment, it can also be expected that the various other formulation components and their concentrations have an influence on the distribution curves.

FIG. 5 shows the distribution values of the previously mentioned pigments in a water-borne paint (Bayhydrol D 155=B) and a solvent-based paint (Larodur BX 150=L) with Cymel 327 and Cymel 1156 as cross-linking resins. The significantly higher distribution value for pigment A in the solvent-based paint compared to the water-borne paint shows that the pigment is dispersed more efficiently in the Larodur 150 BX binder. No marked improvement can be seen for the other two pigments.

Figure 6:
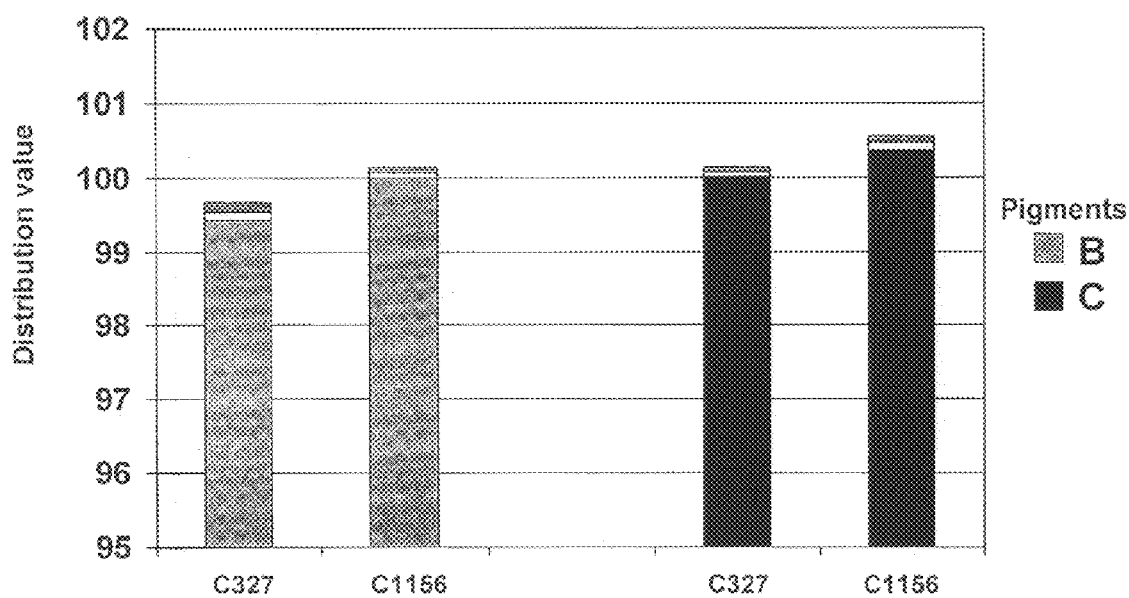
FIG. 6 shows effect of different cross linking resins on distribution values.

FIG. 6 illustrates the distribution values of pigments B and C in a formulation based on Larodur 150 BX as the binder and with Cymel 327 and Cymel 1156 as cross-linking resins.

If Cymel 325 is replaced by Cymel 1156 as the cross-linking resin, the distribution value is seen to rise, regardless of the pigment. This higher distribution values suggest that there has been a shift in the particle size distribution towards finer particle sizes.

Figure 7:
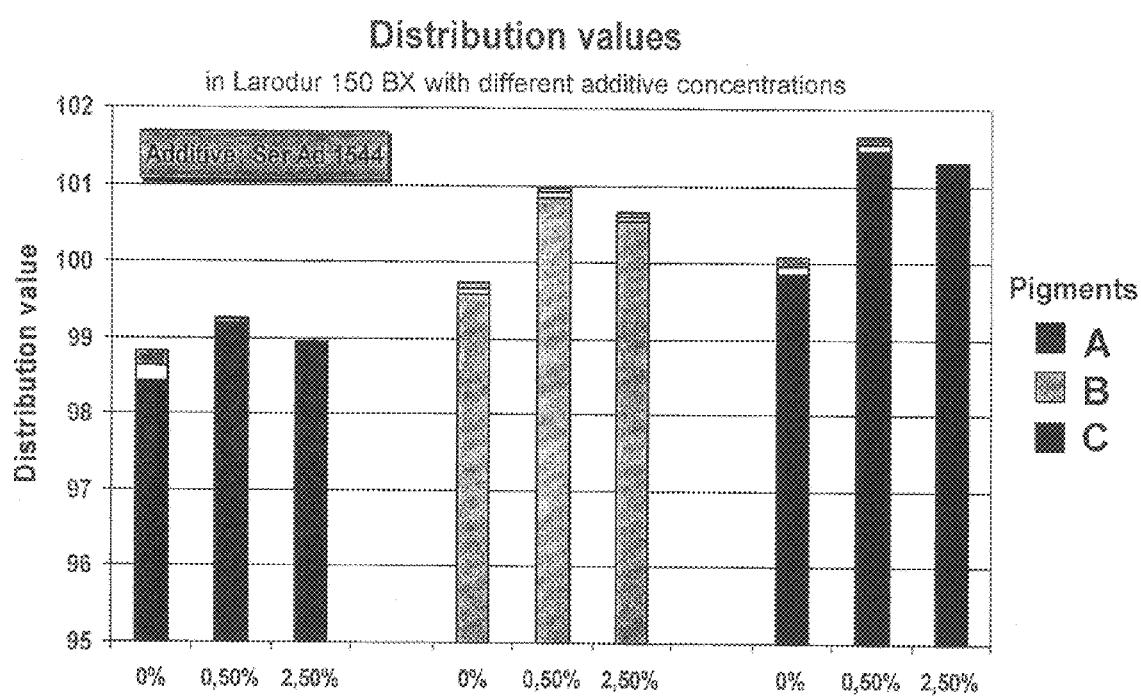
FIG. 7 shows effect of different concentrations of Ser Ad 1544 on distribution values.

Dispersing agents are expected to help achieve optimum distribution of the pigment in the matrix. This effect was studied using a number of additives, including Ser Ad 1544. The result is presented in FIG. 7: The addition of 0.5% Ser Ad 1544 significantly increases the fineness (distribution value) of all the pigments, compared to the coatings without additive. If 2.5% additive is used, the effect is less than after adding 0.5%. However, the distribution values with 2.5% additive are still higher than those for the coating without additive. The dispersing effect of the additive is more pronounced with pigments B and C than with pigment A.

Based on these results, a series of concentrations can be tested in order to determine the optimum additive concentration and select the best additive for a given pigment.

When paints are stored, the state of dispersion of the pigments can change as a result of flocculation, secondary wetting and other processes.

Application of the paints once again subjects them to shear stresses and may possibly reverse any flocculation and sedimentation processes that have occurred. If the same paint is applied in different ways, this can have an effect on the distribution of the pigment in the coating and thus on the properties of the coating.

Figure 8:
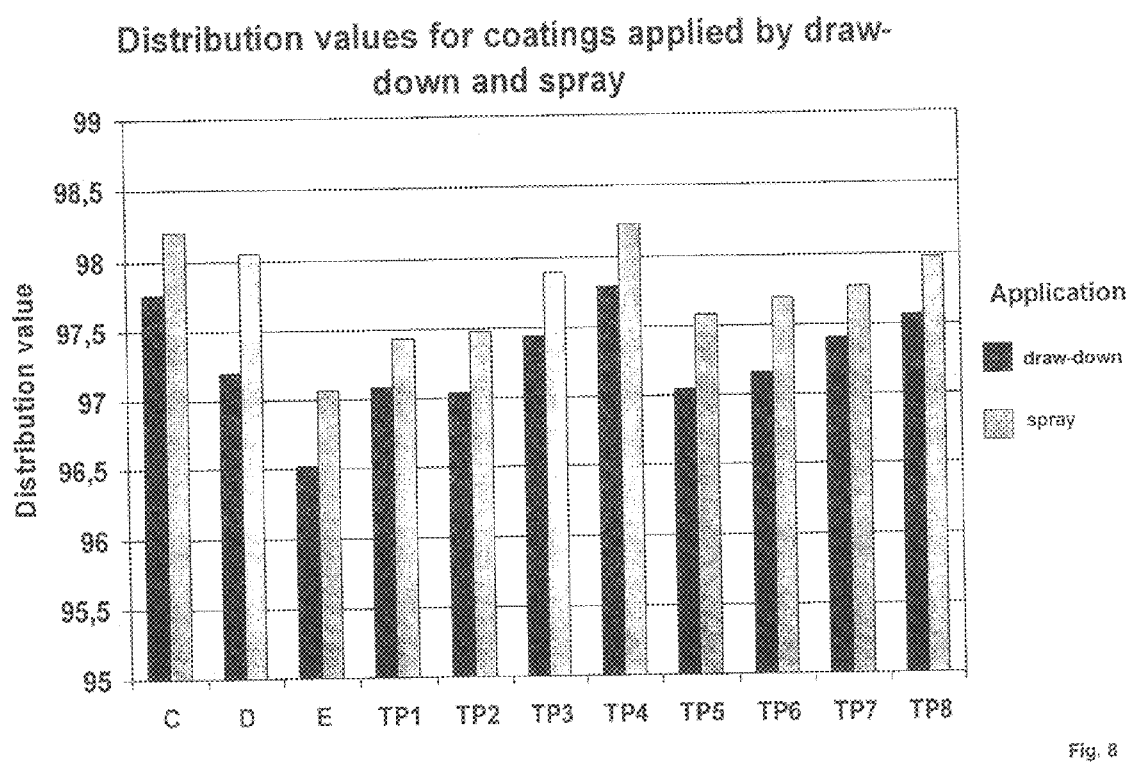
FIG. 8 shows distribution values for spray gun and doctor blade coatings.

FIG. 8 shows the distribution values for coatings applied with a spray gun and coatings applied using a doctor blade (draw-downs) with KRONOS guide formulation R-ACW3 (Larodur 150 BX/Maprenal MF 800).

The tests mainly concentrated on trial pigments (identified as TP) that differ as regards the manner of application of the surface-treatment substances. All the sprayed coatings display higher distribution values, i.e. finer pigment distributions, that the draw-down coatings.

Spraying presumably results in redispersion of previously formed floccules, this not being the case with the drawdowns. This results in a finer pigment distribution in spray application.

The method presented here can be used to examine the effects of changes in the formulation components, the influence of the process during paint production and coating application, as well as the storage stability of the paints, on the distribution of the TiO2 pigments in solid, white coatings.

Based on the knowledge gained, formulations can be optimised in such a way as to improve the distribution of the TiO2 pigment and thus increase the cost-efficiency of the coating.

Initial trials have indicated that the method described also appears to be suitable for testing wet coatings, meaning that any drying and film-forming processes can also be observed.

Moreover, coating properties, such as brightness, tone, hiding power or weather resistance5, can be directly ascribed to changes in the pigment distribution.

Obviously, many modifications and variations of the present invention are possible in light of the above teachings. It is therefore to be understood that, within the scope of the appended claims, the invention may be practiced otherwise than as specifically described.

I claim:

1. A method of estimating the quality S of distribution of TiO$_2$ pigment in a matrix, comprising:
    a) measuring $F_1$, the reflectivity of light from the pigment in the matrix integrated over a first wavelength band from $\lambda_1$ to $\lambda_m$;
    b) measuring $F_2$, the reflectivity of light from the pigment in the matrix integrated over a second wavelength band from $\lambda_n$ to $\lambda_2$, and;
    b) calculating S as a function of $F_1$ and $F_2$.

2. The method of claim 1, where the first wavelength band and the second wavelength band are very broad wavelength bands.

3. The method of claim 2, where $\lambda_1 < \lambda_m = \lambda_n < \lambda_2$.

4. The method of claim 3, where $\lambda_1$ is approximately 380 nm and $\lambda_2$ is approximately 720 nm and $\lambda_m$ is approximately 560 nm.

5. The method of claim 4, where S is proportional to $F_1/F_2$.

6. The method of claim 5, where the matrix is a solid matrix.

7. The method of claim 5, where the matrix is a liquid matrix.

8. The method of claim 1, where S is proportional to $F_1/F_2$.

9. The method of claim 1, where the first wavelength band and the second wavelength band are narrow wavelength bands.

10. The method of claim 9, where light of the first wavelength band and the second wavelength band are provided by light emitting diodes (LED's).

11. The method of claim 10, where $\lambda_1 < 440$ nm and 900 nm$< \lambda_2$.

12. The method of claim 9, where light of the first wavelength band and the second wavelength band are provided by semiconductor lasers.

13. The method of claim 9, where the matrix is a solid matrix.

14. The method of claim 9, where the matrix is a liquid matrix.

15. The method of claim 1, further comprising comparing S with the quality of distribution measured for a standard pigment in a standard matrix measured under the same conditions as steps a) and b).

16. A method of estimating the quality S of distribution of TiO$_2$ pigment in a matrix, comprising:
    a) measuring the reflectivity of a first coating of the TiO$_2$ pigment in the matrix as a function of wavelength from a wavelength $\lambda_1$ to a wavelength $\lambda_2$, where $\lambda_1 < \lambda_2$;
    b) determining the wavelength $\lambda_m$ of the maximum value the reflectivity of a coating of the TiO$_2$ pigment in the matrix, where $\lambda_1 < \lambda_m < \lambda_2$;
    c) determining $F_1$, the reflectivity of light from the pigment in the matrix integrated over the wavelength band from $\lambda_1$ to $\lambda_m$;
    d) determining $F_2$, the reflectivity of light from the pigment in the matrix integrated over the second wavelength band from $\lambda_m$ to $\lambda_2$; and
    e) calculating $S = F_1/F_2$.

17. The method of claim 16, where a second coating is prepared and steps a), c), d) and e) are followed using $\lambda_m$ of the first coating, and the quality values of the first and the second coating are compared.

* * * * *